United States Patent
Krajewski et al.

(10) Patent No.: US 6,475,178 B1
(45) Date of Patent: Nov. 5, 2002

(54) AUTOPRIMING A MICRO-CASSETTE WHILE MINIMIZING THE FORMATION OF AIR BUBBLES IN A PUMPING CHAMBER

(75) Inventors: David J. Krajewski, Hollister, CA (US); Thomas D. Canup, San Jose, CA (US)

(73) Assignee: Abbott Laboratories, Abbott Park, IL (US)

( * ) Notice: Subject to any disclaimer, the term of this patent is extended or adjusted under 35 U.S.C. 154(b) by 134 days.

(21) Appl. No.: 09/636,338

(22) Filed: Aug. 10, 2000

(51) Int. Cl.[7] .......................... A61M 1/00; F04B 23/08
(52) U.S. Cl. .......................... 604/31; 604/67; 604/123; 417/199.2
(58) Field of Search .......................... 604/31, 67, 123; 417/199.2, 28

(56) References Cited

U.S. PATENT DOCUMENTS

| | | | |
|---|---|---|---|
| 5,262,068 A | * 11/1993 | Bowers et al. | 417/199.2 X |
| 5,496,273 A | 3/1996 | Pastrone et al. | |
| 5,713,865 A | * 2/1998 | Manning et al. | 604/123 X |
| 5,951,870 A | 9/1999 | Utterberg et al. | 210/645 |

* cited by examiner

Primary Examiner—William Wayner
(74) Attorney, Agent, or Firm—Beth A. Vrioni (57) ABSTRACT

A pump used to infuse a medical liquid into a patient is autoprimed under the control of a microprocessor that monitors and adjusts a priming sequence to minimize the accumulation of small air bubbles within a pumping chamber of the cassette. Small air bubbles can be created by the agitation of liquid and air within the cassette during priming, and as a result of changing pressure conditions within the cassette. Adherence of the air bubbles on the walls of the pumping chamber can negatively affect performance of the pump. The microprocessor controls the flow of liquid into the pump cassette from a liquid supply to establish a layer of liquid at the bottom of the air trap, thereby preventing air bubbles within the air trap from moving into the pumping chamber. The layer of liquid acts as a one-way valve, allowing air to rise up from the pumping chamber and pass through the liquid layer into the air trap, but preventing air from passing through the liquid layer and down into the pumping chamber. The microprocessor then back primes the cassette until air is removed from the proximal liquid line connecting the liquid supply to the cassette. At that point, liquid is pumped from the liquid supply to forward prime the cassette until air is removed from the pumping chamber and a distal liquid line.

23 Claims, 4 Drawing Sheets

AUTOPRIMING A MICRO-CASSETTE WHILE MINIMIZING THE FORMATION OF AIR BUBBLES IN A PUMPING CHAMBER

FIELD OF THE INVENTION

The present invention generally relates to a method and apparatus for autopriming a cassette used in a positive displacement volumetric infusion pumping system, and more specifically, to a method and apparatus for minimizing the accumulation of air bubbles in the cassette during the autopriming operation.

BACKGROUND OF THE INVENTION

Various types of pumps are used by medical personnel to infuse drugs into a patient's body. Of these, cassette infusion pumps are often preferred because they provide a more accurately controlled rate and volume of drug infusion than other types of infusion pumps. A cassette pump typically employs a disposable plastic cassette coupled in a liquid line extending between a drug reservoir and the patient's body. The cassette is driven by a pump to infuse liquid from the reservoir through the liquid line.

In one prior art design of a cassette infusion pump, the cassette comprises a plastic shell or housing having a front section joined to a back section. A thin elastomeric sheet or membrane is encapsulated between the two sections. Liquid flows from the reservoir through an inlet port into a pumping chamber defined between the elastomeric membrane and a concave depression formed in the housing. The cassette is inserted into an appropriate receptacle in a pump chassis that typically includes a microprocessor controller and a motor or solenoid-actuated driver. A plunger actuated by the motor or solenoid in the pump driver displaces the elastomeric membrane into the pumping chamber to force liquid from the pumping chamber through an outlet port under pressure. The pump chassis thus provides the driving force that pumps liquid through the cassette. The microprocessor control is programmable to deliver a selected volume of liquid to the patient at a selected rate of flow. In addition, the pump chassis normally includes one or more pressure sensors and air bubble sensors for monitoring and controlling the drug infusion process to protect against potential problems that may arise during the drug delivery.

Many prior art pump systems require manual priming procedures whenever the system is initially connected to the reservoir or supply of liquid, and then again, if a new liquid supply is connected, or if an exhausted liquid supply is replaced. The purpose of priming a pumping system is to ensure that it functions properly, and more importantly, to ensure that air bubbles that can be trapped in a liquid line when initially connected to the cassette do not enter a patient's bloodstream, since air bubbles can have potentially harmful consequences. However, manual priming procedures are time consuming and labor intensive, and often must be performed by a doctor or nurse, which tends to drive up medical costs. Autopriming systems, such as the system described in commonly assigned U.S. Pat. No. 5,496,273, are known in the prior art.

A common method for priming an infusion pump is to ensure that the distal end of the liquid line is disconnected from the patient, and to actuate the pump until no air is observed in the liquid being distally discharged from that end of the liquid line. While this priming technique is effective, a significant amount of liquid must be used to prime the system. In medical environments, the liquid is often a medical solution containing expensive drugs, and sterility concerns prevent the reuse of the liquid discharged during priming. For this reason, a back priming technique is useful to minimize the amount of liquid lost during priming. Back priming involves introducing liquid into the pump from the liquid supply, and then causing the pump to force the liquid to flow in the reverse direction (proximally), which causes air from the pump to be discharged into the liquid supply. This air travels up through the liquid in the liquid supply and rises to a head space within the top of the container. Back priming is only possible when the volume of liquid that can be moved by a single stroke of the pump is greater than the volume of the liquid line leading from the proximal inlet port of the pump to the liquid supply. By employing back priming, it is possible to minimize waste of the liquid caused by discharging liquid from the distal liquid line that is disconnected from the patient.

While prior art methods of autopriming have been able to remove the majority of air contained within a pump and its associated liquid lines, the autopriming process can generate micro bubbles of air in the liquid during the priming process. This problem arises because during the priming cycles, the agitation of the liquid/air mixture within the pump and the changes in pressure conditions within the pump incident to the pumping process cause small air bubbles to be formed. The surface tension along the internal walls of the cassette can capture a significant volume of these small air bubbles, and removing these bubbles in the priming process is difficult. Over a period of time, such bubbles can coalesce to form larger bubbles and are thus undesirable. Bubbles contained in the air trap of a pump cassette pose little problem, as the purpose of the air trap is to retain bubbles entrained in the liquid being delivered by the pump, and any micro air bubbles adhering to the walls of the air trap are likely to rise to the top of the air trap and be prevented from exiting the pump. However, air bubbles formed in, or migrating to, the pumping chamber of a cassette are more problematic. Such bubbles affect the accuracy of the pumping process, as their presence slightly alters the available liquid volume of the pumping chamber. Furthermore, air bubbles in the pumping chamber can become entrained in the liquid being pumped into the patient. While the relative volume of these bubbles is small, thereby presenting little real risk to the patient, clearly, it would be desirable to provide a method for minimizing the accumulation of air bubbles in the pumping chamber of a cassette pump during an autoprime sequence.

Preferably, such a method would prevent air bubbles from migrating from the air trap to the pumping chamber during the autopriming process, but would allow air bubbles from the pumping chamber to escape into and be retained in the air trap. Such a method would preferably be adaptable to existing pump systems without necessitating additional components, but instead, accomplished by requiring only software modifications. Such a method should preferably employ an empirically determined algorithm that uses real-time measurements of the presence of air within the pump cassette to control the autopriming process in response to conditions within the cassette. The prior art does not provide an autopriming algorithm that minimizes the migration of air bubbles into the pumping chamber of a pump cassette.

SUMMARY OF THE INVENTION

In accord with the present invention, a method is defined for priming a cassette pump used for infusing a liquid into a patient so as to minimize the migration of air bubbles into a pumping chamber of the cassette. The method includes the steps of forming a layer of liquid in an air trap of the cassette such that the layer of liquid separates the air trap from the pumping chamber, and back priming the cassette until air is removed from the proximal volume of the system. The cassette is then forward primed until air is removed from the pumping chamber and a distal volume of the system.

In one embodiment, air is removed from the proximal volume by introducing liquid into the cassette and pumping the liquid in a proximal direction until no air is detected by a proximal air sensor within the cassette. Air is then removed from the pumping chamber and distal volume by introducing additional liquid into the cassette and pumping the additional liquid in a distal direction until a desired volume of liquid is distally delivered.

In one embodiment, the liquid layer is created by introducing a full stroke of liquid into a disposable cassette during each pump cycle, until a proximal air sensor within the cassette senses liquid. During the introduction liquid caused by that full stroke, air is distally expelled from the disposable cassette. Pumping is stopped at that point in the pump cycle. More than a full stroke of liquid is delivered into the cassette during the next pump cycle. Preferably, the latter step delivers a volume of liquid that approximates the interior volume of the air trap.

In another embodiment, back priming is accomplished by introducing liquid into the cassette, and pumping that liquid in a proximal direction until no air is detected by a proximal air sensor within the disposable cassette, using full pump strokes of liquid during each pump cycle. Preferably, back priming continues until no air is detected by the proximal air sensor, and then one additional full pump stroke of liquid is back primed to ensure that any air within the proximal volume is discharged into a liquid supply that is in fluid communication with the proximal volume. For back priming to be successful, the volume of a full pump stroke of liquid should exceed the proximal volume.

With respect to forward priming and removing air from the pumping chamber and the distal volume, in one embodiment, a full pump stroke of liquid is distally delivered in each pump cycle. In another embodiment, if the distal volume exceeds the volume of a full pump stroke of liquid, after a full pump stroke of liquid is delivered, the next pump stroke is modified to deliver only enough liquid to make up the difference between a full pump stroke of liquid and the distal volume. In yet another embodiment, when the distal volume is less than the volume of a full pump stroke of liquid, forward priming is accomplished by using a full pump stroke of liquid. In still another embodiment, when the distal volume is less than the volume of a full pump stroke of liquid, forward priming is accomplished by using a partial pump stroke of liquid.

Preferably, the pump being primed includes a housing that defines a liquid path between an inlet port adapted to couple in fluid communication with a source, and an outlet port adapted to couple in fluid communication with an infusion site on the patient. Also, the pump preferably includes an inlet air sensor that produces a signal indicative of air being detected proximate to the inlet port, the liquid path including a pumping chamber covered by an elastomeric membrane that when forced into the pumping chamber by a driven member, displaces the liquid from the pumping chamber through one of the inlet port and the outlet port; and an air trap that is preferably disposed between the inlet air sensor and the pumping chamber. By introducing sufficient liquid into the air trap of the cassette, a layer of liquid separates the interior volume of the pumping chamber from the interior volume of the air trap, acting as a one-way valve that allows air from the pumping chamber to pass into the air trap, while preventing air from the air trap from passing into the pumping chamber. Preferably, the layer of liquid substantially covers the bottom of the air trap. In one embodiment, the layer of liquid is established by pumping in a forward direction, using strokes that deliver a standard volume of liquid in each pump cycle, until the inlet air sensor does not detect air; and then pumping one additional cycle in the forward direction, using an extra long stroke that delivers a larger than standard volume of liquid in the additional cycle(s). Preferably, the volume delivered by the extra long stroke(s) substantially equals the interior volume of the air trap. In another embodiment, the volume delivered by the extra long stroke(s) is empirically determined to generate a layer of liquid within the air trap that is of a desired size.

Another aspect of the present invention is directed to apparatus that includes elements that perform functions generally consistent with the steps implemented by the method described above.

BRIEF DESCRIPTION OF THE DRAWING FIGURES

The foregoing aspects and many of the attendant advantages of this invention will become more readily appreciated as the same becomes better understood by reference to the following detailed description, when taken in conjunction with the accompanying drawings, wherein.

DESCRIPTION OF THE PREFERRED EMBODIMENT

Overview of the Present Invention

The present invention employs an algorithm to minimize the migration of air bubbles from an air trap into a pumping chamber in the cassette of an infusion pump during an autopriming sequence. One preferred embodiment of the present invention will be incorporated in Abbott Laboratories' PLUMA+™ Infusion Pump, which will be used in conjunction with its PLUM™ Cassette. An algorithm used in this embodiment employs variables that have been empirically determined for these specific products. However, it should be noted that a similar algorithm can use variables empirically determined for other designs of infusion cassettes and cassette pumps. Thus, it is not intended that the present invention be in any way limited to the specific design of the pump and cassette discussed below.

The terms "proximal" and "inlet" as used herein in connection with the following description and the claims that follow synonymously refer to a portion of the cassette that is adapted to connect to a liquid line or lines, each liquid line being coupled in fluid communication with a liquid supply or reservoir of liquid. The terms "distal" and "outlet" similarly synonymously refer to a portion of the cassette that is adapted to connect to a liquid line in fluid communication with a patient. The term "back prime" or "back priming" should be understood to refer to operating a pump such that liquid and/or air are pumped in the proximal direction, delivering the liquid and/or air to the liquid supply, rather than to the patient. Similarly, "forward prime" or "forward, priming" should be understood to mean operating a pump such that liquid and/or air are pumped in the distal direction, such that the liquid and/or air are delivered to the outlet of the pump. It should be noted that during priming, the distal liquid line is temporarily disconnected from a patient to prevent air from being infused into the patient's body. The term "proximal volume" should be understood to mean the volume of the portion of the liquid path that begins at the liquid supply and ends at a proximal air sensor in the cassette. The term "distal volume" should be understood to mean the volume of the portion of the liquid path that begins at a distal air sensor in the cassette and ends at the distal outlet (end) of the distal liquid line. It should be noted that terms such as "fluid line" and "fluid supply" are often used in association with pumps, and that the term "fluid" generally means either a gas or a liquid (or a mixture of gas and liquid). In this specification, the terms "liquid line" and "liquid supply" have been used, rather than the broader terms "fluid line" and "fluid supply", because ideally the material provided by the supply source and flowing through the lines and the pump is a liquid, rather than a gas or a mixture of gas and liquid. It should be understood that in the unprimed state, air will be inside the proximal and distal lines, even though these lines are referred to as liquid lines. However, once the system is properly primed, the fluid flowing though these lines and the pump will be a liquid (with little air or no air entrained within the liquid), hence the use of the term "liquid" versus "fluid".

Since the following description of one preferred embodiment of the present invention relates to its use with the PLUM A+ Pump and PLUM Cassette, certain aspects are determined by the operating specifications of this pump. For example, a deliverable volume per pump cycle in this embodiment is from 0–500 $\mu l$, with a preferred volume being about 333 $\mu l$. The cassette volume is 1170 $\mu l$, and the air trap volume within the cassette is 550 $\mu l$. The proximal volume is 305 $\mu l$, while the distal volume is 330 $\mu l$.

In its simplest form, autopriming a pump cassette is the process in which an infusion pump automatically draws a liquid (as a liquid or a mixture of air and liquid) from a liquid source (such as a proximally attached drug container or reservoir), expels the air inside the cassette, and primes the distal line with a volume of liquid. During this process, the agitation and movement of air and liquid within the cassette tends to enable small air bubbles to become trapped in the cassette, by adhering to the walls of the air trap and pumping chamber. The surface tension of the inside walls of the cassette can capture a significant amount of these small air bubbles. Thus, while a significant portion of the air is removed from the cassette in prior art autopriming techniques, a small amount of air is dispersed within the cassette in the form of these small air bubbles. This results in a less than desirable primed cassette. The presence of these small air bubbles in the air trap is of minor consequence, as the volume of the air trap (550 $\mu l$) significantly exceeds the likely aggregate volume of such small air bubbles, and thus during normal pumping operations these small air bubbles remain trapped in the air trap.

However, the presence of these small bubbles in the pumping chamber is more problematic. These bubbles slightly reduce the volume of the pumping chamber available for pumping liquid, and thus slightly less than the desired volume of liquid will be delivered each pumping cycle. Even larger errors are introduced because, during a pumping cycle, pressure conditions within the pumping chamber change. Thus, the total volume of all air bubbles trapped within the pumping chamber does not remain constant, but instead, varies as the pressure within the pumping chamber changes. Even though the total volume of the pumping chamber is known, because the total volume of all air bubbles trapped within the pumping chamber is not constant throughout a pumping cycle, it is impossible to determine with certainty the actual volume of fluid delivered during that pumping cycle. Furthermore, air bubbles within the pumping chamber can escape into the liquid being delivered to the patient. While these air bubbles are small in size and generally do not pose a serious threat, minimizing the amount of such small bubbles in the pumping chamber both enhances accuracy and safety.

While the small air bubbles that are generated in the trap are likely to remain in the trap under normal operating conditions, during priming it is possible for these small air bubbles to migrate from the air trap to the pumping chamber. The solution to preventing this migration, and thereby minimizing the accumulation of these small air bubbles within the pumping chamber, is to establish a layer of liquid at the bottom of the air trap as the priming sequence is begun. This liquid layer acts as a one-way valve. Because the liquids being used are primarily aqueous, the liquids are heavier than air. Thus a layer of liquid at the bottom of the air trap will allow air bubbles from the pumping chamber to ascend through the liquid layer into the air trap, while simultaneously preventing air bubbles in the air trap from descending through the liquid layer into the pumping chamber. Note that the air trap is disposed above the pumping chamber in the Plum A+ cassette, and that this disposition is relatively common in cassette pumps.

Once the liquid layer is in place, the algorithm utilizes back priming and forward priming to expel air from inside the cassette, and then fill the cassette and the distal line with liquid. Success of the algorithm in minimizing the accumulation of these tiny air bubbles in the pumping chamber lies in thoroughly understanding the physical dimensions of the liquid paths within a cassette, and empirically determining the volume of liquid flow required to initially establish the liquid layer separating the air trap from the pumping chamber.

The algorithm consists of three pumping phases:
1) Establishing the liquid layer separating the air trap from the pumping chamber.
2) Back priming to remove air from the air trap and proximal volume.
3) Forward priming to remove air from the pumping chamber and the distal volume.

Further details of the preferred embodiment are as follows.

Details of a Preferred Embodiment

Figures 1, 2:
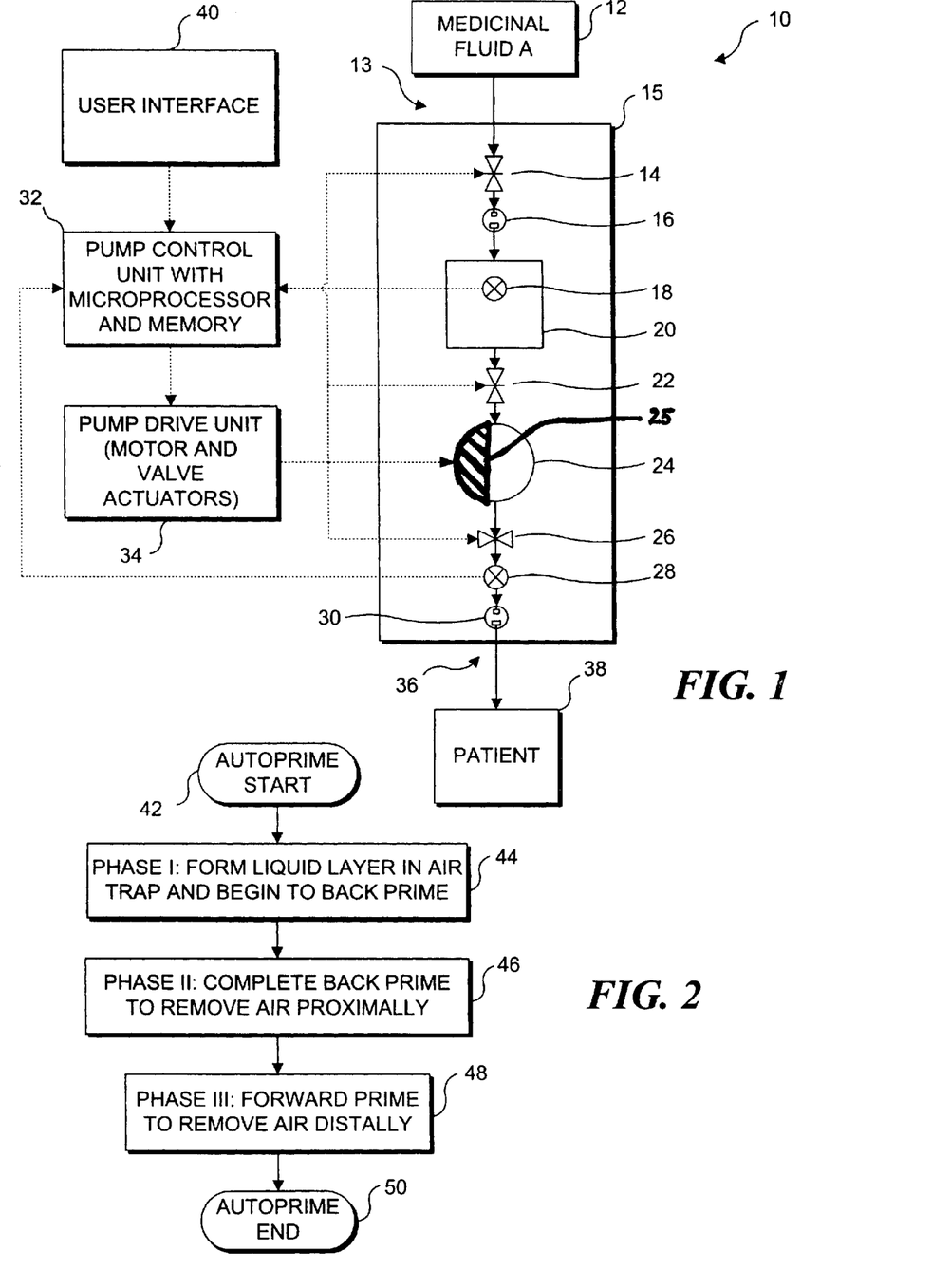
FIG. 1 is a schematic block diagram of a cassette pump system with a cassette that can be autoprimed in accord with the present invention.
FIG. 2 is a flow chart illustrating the logical steps implemented to autoprime the cassette of FIG. 1 using a three-phase process in accord with the present invention.

With reference to FIG. 1, a cassette type infusion pump 10 that implements the present invention is shown. A source 12 of medicinal liquid A is coupled in fluid communication with a proximal end 13 of a cassette 15. The flow of medicinal liquid A into the cassette is selectively controlled by a supply valve 14. It should be noted that additional medicinal liquid sources are often used in conjunction with cassette type infusion pumps, and that the autoprime sequence of the present invention can be used to autoprime a cassette and liquid lines from a plurality of liquid supply sources. With supply valve 14 in the open position, medicinal liquid A flows through an air sensor 16 and into an air trap 20. Such air sensors and air traps are common features of cassette type infusion pumps. The purpose of the air sensor is to detect air bubbles that may be entrained in medicinal liquid A before the liquid is passed on into the pumping chamber and to the patient. Excess air bubbles entering a patient's bloodstream can cause an air embolism with potentially harmful consequences.

A proximal (or inlet) pressure sensor 18 is disposed within air trap 20. Medicinal liquid A exits the air trap through an inlet valve 22, and when the inlet valve is in its open position, flows into a pumping chamber 24. An outlet valve 26 opens to allow medicinal liquid A to exit pumping chamber 24 during the appropriate portion of the pump cycle. It should be noted that in the preferred embodiment, when both the inlet valve and the outlet valve are moving at the same time, the valve that is closing moves first, closely followed by the valve which is opening. Thus, in operation the outlet valve will close and the inlet valve will open (or the inlet valve will close and the outlet valve will open) rather than the inlet valve opening, followed by the outlet valve closing.

Cassette style infusion pumps are constant displacement pumps. The volume of medicinal liquid in pumping chamber 24 is therefore generally the same for each pump cycle. As noted above, the preferable delivery volume of the medicinal liquid contained within pumping chamber 24 is 333 $\mu$l for this particular embodiment. One side of pumping chamber 24 is covered with an elastomeric membrane 25. Infusion on pump 10 includes a pump drive unit 34, which incorporates a prime mover (preferably an electric stepper motor), a plunger driven by the prime mover that acts on the elastomeric membrane 25, and a plurality of valve actuators that control supply valve 14, inlet valve 22, and outlet valve 26 (no drive unit components are separately shown). Medicinal liquid is forced from pumping chamber 24 (when inlet valve 22 is closed and outlet valve 26 is opened) by the action of the drive unit plunger forcing the elastomeric membrane 25 into the pumping chamber to displace the liquid contained therein.

In the preferred embodiment, the plunger position is variable from −489 steps to +220 steps of the stepping motor, where a home position of the plunger is defined to be at 0 steps. A nominal stroke distance of the plunger to deliver 333 $\mu$l of liquid is +169 steps. Inlet valve 22 and outlet valve 26 are formed by the interaction of the elastomeric membrane 25 and a portion of the cassette and are closed when actuator rods (not shown) of drive unit 34 act on the elastomeric membrane 25 to close off flow through a liquid passage of the cassette. Details of the valve mechanisms are not disclosed herein, but are well known to those of ordinary skill in this art. When outlet valve 26 is in its open position, the medicinal liquid forced from the pumping chamber flows through past a distal pressure sensor 28, through a distal air sensor 30, and exits the cassette at a distal end 36 to be conveyed to a patient 38. Details of suitable pressure sensors for use with the present invention and of other aspects of the cassette are disclosed in commonly assigned U.S. Pat. No. 5,554,115, the specification and drawings of which are hereby specifically incorporated herein by reference. Note that while proximal pressure sensor 18, distal pressure sensor 28, and distal air sensor 30 are elements of the Plum A+ cassette, these elements are not required for practicing the present invention.

Infusion pump 10 also includes a user interface 40 and a control unit 32. The control unit preferably includes a microprocessor and a memory (not separately shown); however, it will be understood that the control unit can alternatively use other types of logic devices for implementing the algorithm, such as a hardwired logic control, an application specific integrated circuit (ASIC), etc. The algorithm is stored as a plurality of machine language instructions and data within the memory, and is activated when a user enters a command via user interface 40 to initiate the autoprime sequence for infusion pump 10. The machine language instructions causes the microprocessor of control unit 32 to receive and monitor information from proximal air sensor 16, and to implement the autopriming sequence for the infusion pump.

Accumulation of air bubbles within the pumping chamber is minimized in the present invention by establishing a layer of liquid that separates the air trap and the pumping chamber, and thereafter primes the cassette by controlling the movement of the plunger, and the operation of the inlet and outlet valves. FIG. 2 is a flow chart illustrating the logical steps implemented to autoprime the cassette pump system of FIG. 1, using a three-phase process. The process is initiated at a block 42 by a user entering a start autoprime command via user interface 40. It should be noted that before starting any priming sequence of an infusion pump, the user must ensure the distal liquid line connected to distal end 36 of the pump system is not connected to a patient. During the priming process, air within the pump will be forced from the distal end of this liquid line and must not be infused into the patient's body. Preferably, user interface 40 will prompt a user to verify that the infusion pump is not connected to a patient before initiating the autopriming sequence, and will also prompt the user to confirm that the liquid line has been reconnected to the patient upon completion of the autopriming sequence.

Most infusion pump systems include air and pressure sensing alarms, and preferably such alarms are disengaged during the autopriming sequence. The logic proceeds to a block 44, in which the microprocessor executes Phase I of the sequence to establish a layer of liquid at the bottom of the air trap in order to separate the air trap from the pumping chamber. The logic then proceeds to a block 46, and the logic executes Phase II of the algorithm, and in which the pump reverses the direction of the fluid flow and back primes until there is no air in air trap 20 or in the proximal liquid line. The logic then proceeds to a block 48, and executes Phase III of the algorithm, in which pump system 10 reverses direction yet again, and forward primes to remove air from the pumping chamber and to fill the distal liquid line. After completing Phase III, the logic proceeds to an end block 50, and the autoprime sequence is complete.

Figure 3A:
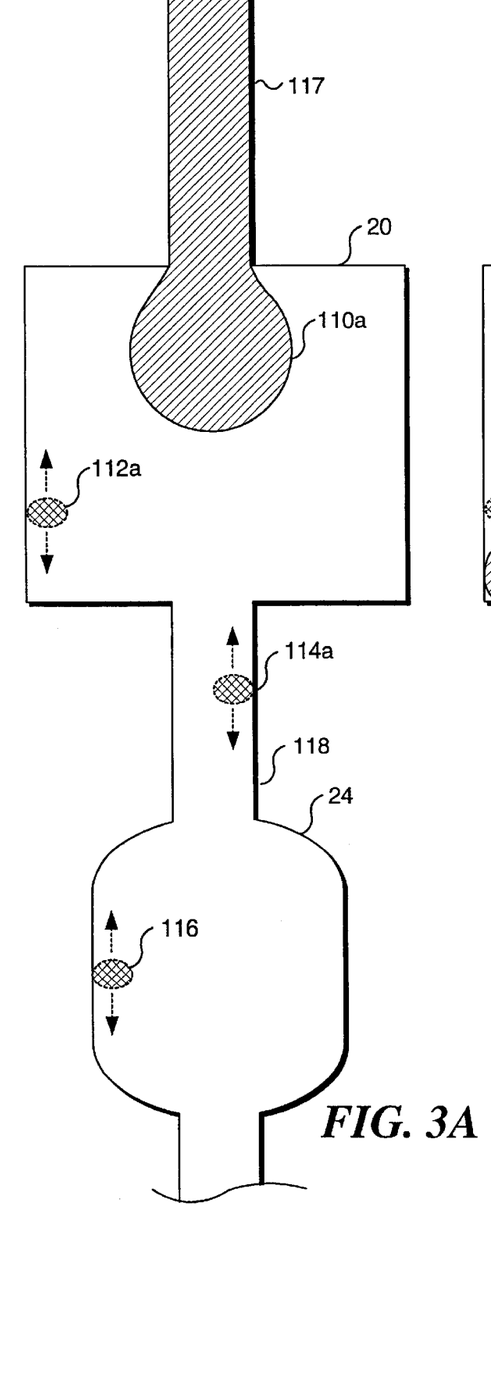
FIGS. 3A and 3B are schematic views illustrating the formation of a liquid layer at the bottom of air trap in the cassette of FIG. 1.
Figure 3B:
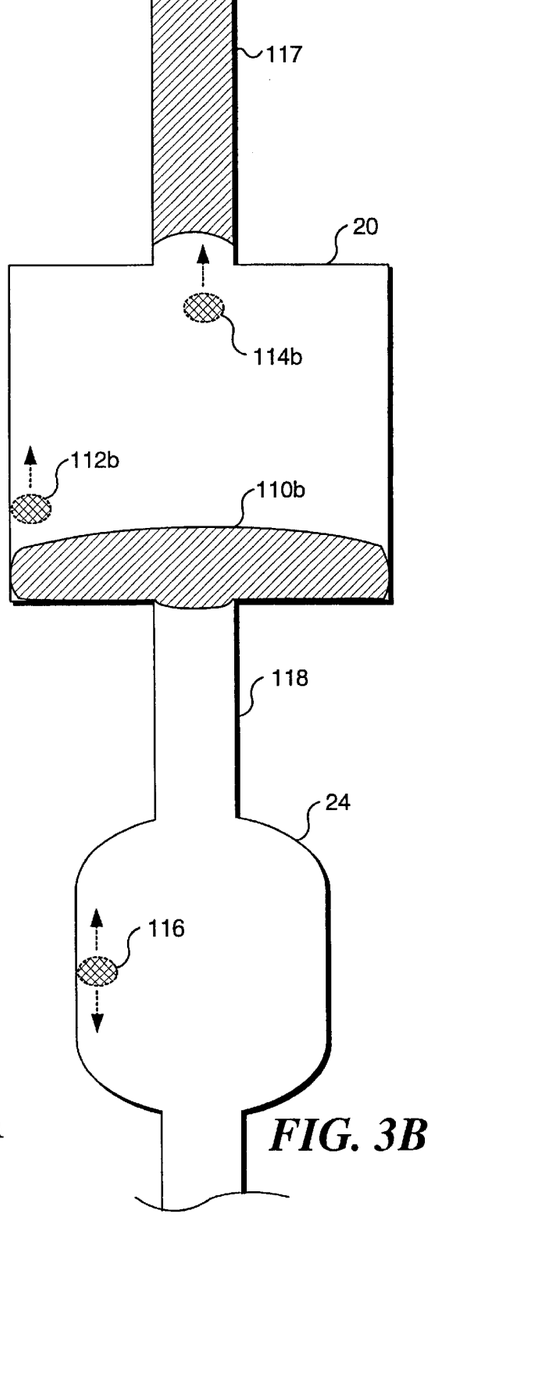

FIGS. 3A and 3B are schematic views showing a liquid 110a entering air trap 20 from the proximal liquid line and forming a liquid layer 110b that separates the air trap from pumping chamber 24. It should be noted that inlet valve 22 (FIG. 2) is disposed in a liquid path 118 between air trap 20 and pumping chamber 24, but has been omitted in FIGS. 3A and 3B, because it is only when inlet valve 22 is in the open position that the liquid layer in air trap 20 is functional to separate the pumping chamber from the air trap. In FIG. 3A, liquid flows from liquid supply 12 (see FIG. 1) through a liquid path 117 to air trap 20. Gravitational and liquid surface tension forces cause a drop 110a to form at the top of air trap 20. Air bubbles 112a, 114a, and 116 adhere to the walls of air trap 20, liquid path 118, and pumping chamber 24, respectively. It should be noted that these air bubbles are shown in phantom view, because at this stage in the priming process, the internal volumes of air trap 20, liquid path 118, and pumping chamber 24 are filled with air, and discrete small air bubbles will not form until those volumes fill with liquid. However, the agitation of the liquid and air within these volumes, combined with the pressure changes accompanying the priming process, will generally produce conditions that favor the creation of such small air bubbles that are generally attracted to the walls of these volumes. Air bubbles 112a, 114a, and 116 are shown with arrows indicating that the bubbles are generally free to move up or down, if the bubbles are dislodged from the volume walls. Note that whether these air bubbles rise or fall depends on gravity, temperature and pressure conditions, and whether a particular bubble becomes entrained in a liquid flow.

In FIG. 3B, gravitational and surface tensional forces have separated drop 110a from the column of liquid in liquid path 117, and the drop has fallen to the bottom of air trap 20, forming liquid layer 110b that generally conforms to the shape of the bottom surface of air trap 20. Because the density of liquid layer 110b is significantly great than that of the air bubbles, the air bubbles that are above liquid layer 110b are prevented from moving below the liquid layer. Thus liquid layer 110b acts as a one-way valve.

Air bubble 116 is free to rise or fall if and when the air bubble 116 becomes detached from the wall of the pumping chamber. However, air bubbles 114b and 112b are not free to pass downwardly through liquid layer 110b due to the differences in density between the air of the bubble and the liquid in the layer. Note that in FIG. 3B, air bubble 114a has become detached from the wall of liquid path 118, and has risen through liquid layer 110b, as an air bubble 114b. But, an air bubble 112b cannot pass down through liquid layer 110b, but instead, when detached, can only move upwardly. Thus, liquid layer 110b prevents air bubbles from migrating out of the air trap into the pumping chamber, yet allows air bubbles from pumping chamber 24 or liquid path 118 to migrate upwardly into the air trap. It is important that drop 110a be large enough to form liquid layer 110b so that the liquid layer substantially covers the bottom surface of air trap 20, to ensure that air bubbles are prevented from migrating into pumping chamber 24 from the air trap. Preferably, the volume of liquid required to ensure that liquid layer 110b is sufficiently large is empirically determined. In the preferred embodiment, a volume of liquid substantially equal to the volume of air trap 20 is introduced into the pump before the back priming and forward priming phases are initiated.

Figure 4:
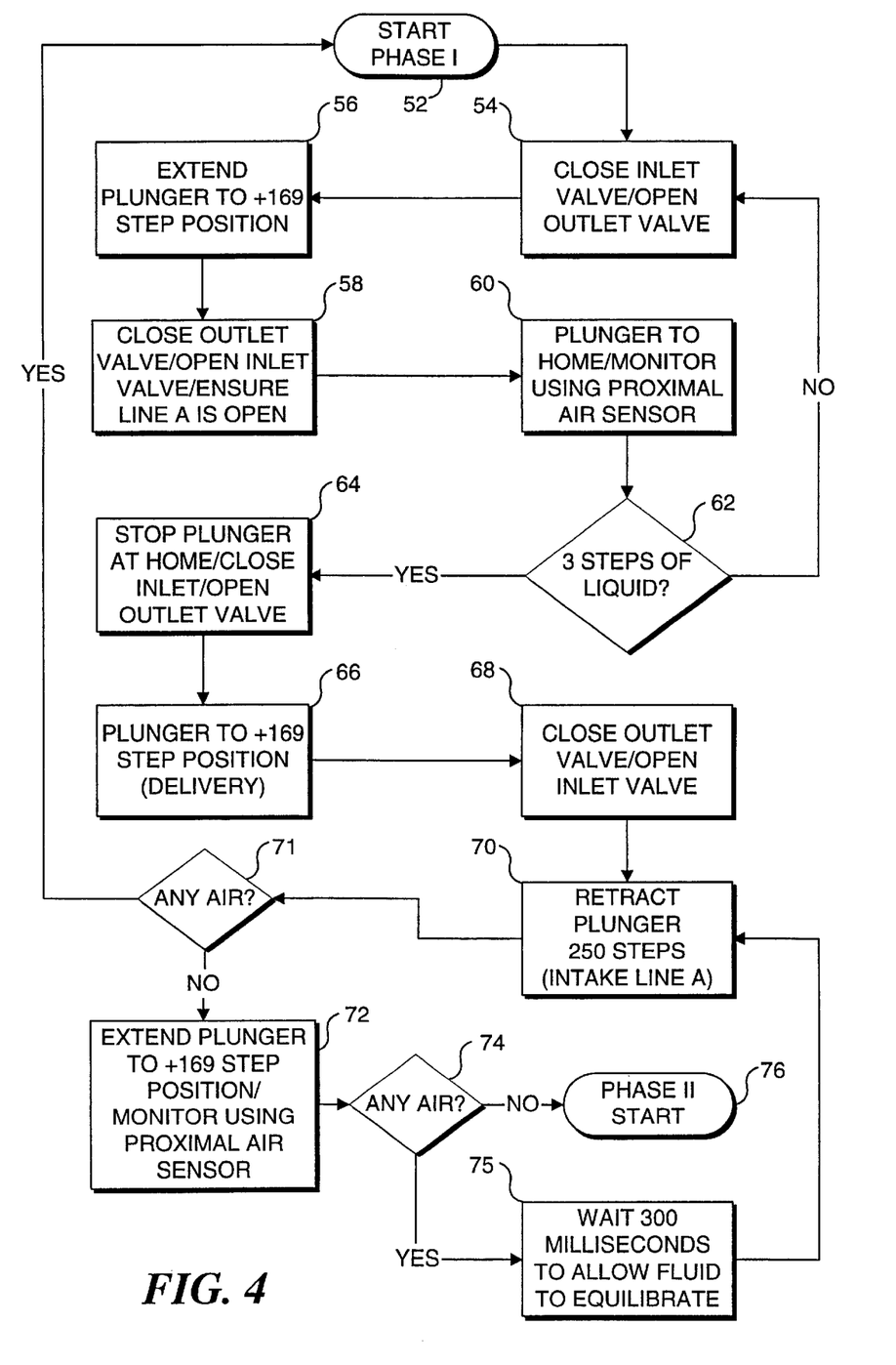
FIG. 4 is a flow chart illustrating the logical steps implemented to complete the first phase of the three-phase process of FIG. 2.

FIG. 4 is a flowchart illustrating the series of logical steps implemented to execute Phase I of the autopriming sequence, the formation of liquid layer 110b. The process begins at a block 52. The logic proceeds to a block 54, and the algorithm instructs pump control unit 32 to close inlet valve 22 and to open outlet valve 26. The logic then proceeds to a block 56, and pump control unit 32 extends the plunger to the +169 step position. As noted above, the plunger is in contact with the elastomeric membrane 25 that forms pumping chamber 24, and as the plunger advances, the elastomeric membrane 25 is displaced, thereby reducing the volume of pumping chamber 24 and expelling air from pumping chamber 24 through open outlet valve 26. The logic then proceeds to a block 58, and pump control unit 32 closes outlet valve 26, opens inlet valve 22, and opens supply valve 14 (if it is not already open). Medicinal liquid A can now flow into the cassette. The logic proceeds to a block 60, where pump control unit 32 retracts the plunger towards the home position while monitoring proximal air sensor 16. The retraction of the plunger and the resulting increase in volume of the pumping chamber create a pressure differential that draws liquid from liquid supply 12 toward the cassette. Control unit 32 is monitoring the proximal air sensor, and the logic moves to a decision block 62. In decision block 62, if at least three "steps" of liquid are seen (i.e., a volume of liquid corresponding to three steps of the stepping motor that actuates the plunger), then the logic proceeds to a block 64, and the plunger retraction is halted. At this point, pump control unit 32 closes inlet valve 22 and opens outlet valve 26. As noted above, a full stroke of the plunger preferably delivers 333 µl of liquid. Movement of the plunger from the home position to the +169 step position represents a full stroke. Thus, a single step of the plunger is equivalent to 333 divided by 169, or 1.97 µl, and three steps of liquid represents approximately 6 µl.

At this point, the proximal volume (i.e., the volume defined by the liquid path from liquid supply 12 to air sensor 16) has been filled with liquid, and the next intake stroke will deliver liquid into air trap 20. Because the proximal volume is a determinable quantity, instead of using an air sensor to determine that the proximal volume has been filled with liquid, the movement of the plunger can be stopped after the number of steps equivalent to the proximal volume have been completed (based on 1.97 µl/step, or whatever the ratio is for the particular type of pump to which the present invention is applied). This alternative is particularly useful if the pump cassette being used does not incorporate a proximal air sensor. It should be noted that the plunger movement is halted once the proximal volume is filled with liquid, to ensure that the next pump cycle will deliver sufficient liquid to form liquid layer 110b.

As noted above, it is critical that the size of drop 110a be controlled to ensure that liquid layer 110 is of sufficient volume able to prevent air bubbles from migrating to pumping chamber 24 from air trap 20. Rather than simply controlling the volume of liquid delivered, it is preferable to control the size of the drop, so that the liquid layer at the bottom of air trap 20 is composed of a single contiguous layer, rather than a layer formed by a plurality of small drops. While a plurality of small liquid drops would similarly prevent the migration of air bubbles from above the plurality of liquid drops into the pumping chamber, small air bubbles can be trapped on the bottom of the air trap at the interstices of the plurality of small liquid drops. These trapped small air bubbles might then migrate into the pumping chamber, because they are already beneath the liquid layer. Thus, it is preferably that liquid layer 110b be formed from a single drop 110a in a single pump cycle, rather than from a plurality of smaller drops delivered over a plurality of pump cycles. By ensuring that the distal side of air trap 20 is coated with a single contiguous drop of liquid, the algorithm ensures that no air bubbles are entrained between multiple drops of liquid.

As liquid enters into air trap 20, many factors affect the size of droplet that will be formed. These factors include the viscosity and surface tension of the liquid, the physical dimensions of the liquid path and the air trap, the effect of gravity, and the volume of liquid introduced into the air trap. These parameters are determinable, such that a preferred size of droplet can be calculated. The calculated value can then be tested empirically. Empirical tests of the preferred embodiment applied to a Plum A+ cassette and pump have shown that once three steps of liquid have been monitored by proximal air sensor 16, a drop of the desired size and volume can be formed at the bottom of air trap 20 if the next pump cycle delivers a volume of liquid equivalent to 250 steps of the plunger (which is approximately 500 $\mu l$, and approximately equal to the volume of air trap 20).

Referring once again to decision block 62, if proximal air sensor 16 has not monitored three steps of liquid by the time that the plunger has returned to the home position, the logic then returns to block 54, and the logical steps described by blocks 54, 56, 58, and 60 are repeated until three steps of liquid have been detected. Once three steps of liquid have been monitored by proximal air sensor 16, the logic proceeds to a block 64.

As noted above, in block 64 pump control unit 32 stops the retraction of the plunger towards the home position, closes inlet valve 22 and opens outlet valve 26. At this point, no drop of liquid has been formed in air trap 20, but the proximal volume has been filled with liquid. Because inlet valve 22 is in its closed position, the liquid in the proximal volume is prevented from moving in this portion of the autoprime sequence. The logic then proceeds to a block 66, and the plunger is advanced to the +169 step position. At this point, the plunger and pumping chamber are preparing for the intake stroke in the pump cycle, which will draw additional liquid into the pump.

The logic then proceeds to a block 68, in which pump control unit 32 closes outlet valve 26 and opens inlet valve 22. The logic proceeds next to a block 70, and the plunger is retracted. At this time, the plunger is retracted from +169 steps to −81 steps (for a total movement of 250 steps). This movement of the plunger corresponds to an extra long intake stroke, as discussed above, and air trap 20 should be almost completely full of liquid, ensuring that a sufficient liquid layer 110*b* exists to prevent air bubbles from migrating into pumping chamber 24. The logic then proceeds to a decision block 71.

At block 71, proximal air sensor 16 determines if any air has been detected. If air has been detected, the logic loops back to block 52, and the logical steps represented by blocks 52–71 are repeated until no air is detected. If no air has been detected, the logic proceeds to a block 72, and pump control until 32 extends the plunger to the +169 step position, while monitoring for liquid and air using proximal air sensor 16. Because outlet valve 26 is in its closed position, the advancing plunger acts on the elastomeric membrane 25 forcing air out of pumping chamber 24, past open inlet valve 22, and through liquid layer 110*b* in a proximal direction. This operation is "back priming."

The logic then proceeds to a decision block 74, and proximal air sensor 16 once again determines if any air has been detected. If no air has been detected, the logic proceeds to a block 76, completing Phase I, and pump control unit 32 initiates Phase II. If air has been detected, the logic loops back to block 70 through block 75, whereby the pump control unit 32 waits 300 milliseconds to allow fluid to equilibrate. The logical steps represented by blocks 70–75 are repeated until no air is detected.

Figure 5:
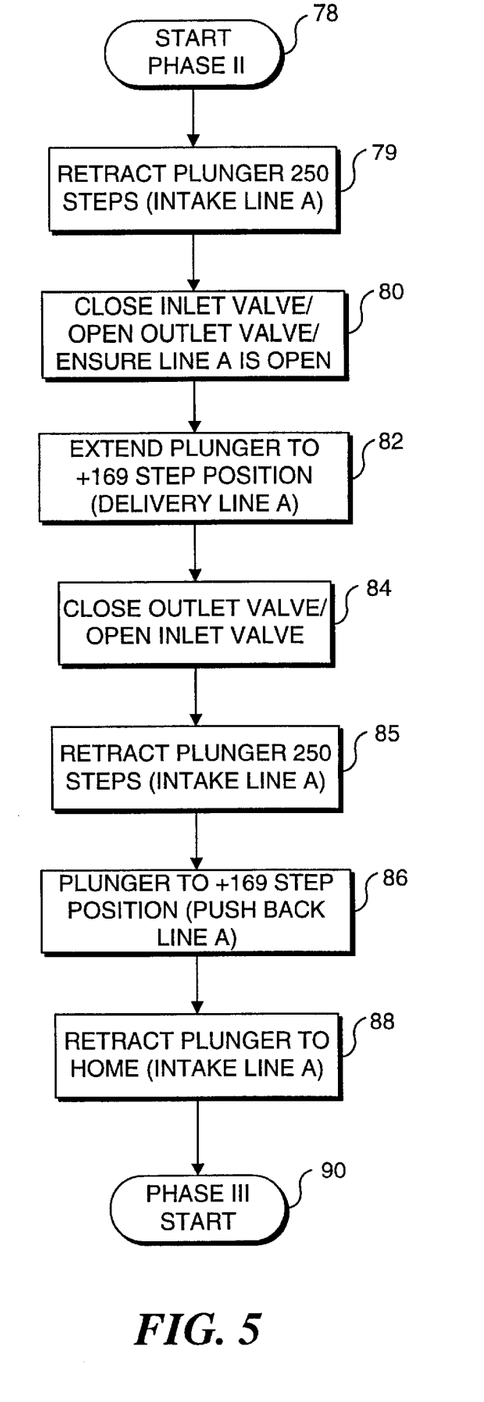
FIG. 5 is a flow chart illustrating the logical steps implemented to complete the second phase of the three-phase process of FIG. 2.

FIG. 5 illustrates the logical steps implemented to execute Phase II of the autoprime sequence, which continues back priming for one additional pump cycle, to ensure that any air bubbles in the proximal volume (between liquid supply 12 and air sensor 16) are forced out of the proximal volume and into the liquid supply. Once air bubbles are forced into liquid supply 12, they rise through the liquid to a head space with the container for liquid supply 12. It should be noted that for back priming to be effective, the volume of liquid delivered in a single pump cycle should exceed the proximal volume. If it does not, then air can remain in the proximal volume.

For example, if a normal pump cycle delivers 333 $\mu l$ of liquid, and the proximal volume is 400 $\mu l$, then 67 $\mu l$ of the proximal volume will remain unprimed. In the preferred embodiment, the proximal volume is less than 305 $\mu l$, and the delivery volume is 333 $\mu l$, thereby ensuring that all of the proximal volume is primed.

Phase II begins at a start block 78. The logic proceeds to a block 79, wherein pump control unit 32 retracts the plunger. At this time, the plunger is retracted for a total movement of 250 steps (the extra long stroke described above). Note that this plunger retraction represents an intake stroke. Air trap 20 should be completely full of liquid, ensuring that a sufficient liquid layer 110*b* exists to prevent air bubbles from migrating into pumping chamber 24. The logic then proceeds to a block 80, where pump control unit 32 closes inlet valve 22 and opens outlet valve 26 (also ensuring that supply valve 14 is in its open position, as it already should be). The logic then proceeds to a block 82, and pump control 32 extends the plunger to the +169 step position. Note that this results in a movement of 250 steps, not 169 steps, because the plunger was previously retracted 250 steps (see block 79) from the +169 step position (see block 72 of FIG. 4). The logic then moves to a block 84, in which pump control unit 32 closes outlet valve 26 and opens inlet valve 22. The logic proceeds to a block 85, where pump control unit 32 once again retracts the plunger in an extra long stroke, resulting in a total plunger movement of 250 steps. The logic continues at a block 86, where pump control 32 advances the plunger to the +169 step position, which decreases the volume of pumping chamber 24. This movement of the plunger forces any air bubbles in the proximal volume into liquid supply 12. Note air will also be forced from pumping chamber 24 into air trap 20, but because air trap 20 has a significantly larger interior volume than pumping chamber 24 (550 $\mu l$ vs. 333 $\mu l$ for a normal pump stroke), no air will escape air trap 20 by moving in a proximal direction. Thus, without distally delivering any liquid, the proximal volume is fully primed. Furthermore, a liquid layer separates the air trap and the pumping chamber, so that as the pumping chamber and distal volume are primed in Phase III, no air bubbles from the air trap can migrate into the pumping chamber.

After the steps of block 86 have been completed, the logic proceeds to a block 88, in which pump control unit 32 retracts the plunger to the home position. In this step, because inlet valve 22 is in the open position, liquid from liquid supply 12 fills pumping chamber 24. Note that as additional liquid enters the pump, the liquid that forms liquid layer 110*b* will be forced into pumping chamber 24 as additional liquid is drawn into the pump during the intake stroke of block 88. Because all the air in the proximal volume has been removed, a continuous column of liquid flows into the pump, through the proximal volume and air trap, and this liquid enters the pumping chamber. Thus, the liquid that had formed liquid layer 110*b* is replaced by additional liquid, and air bubbles will still be prevented from migrating into the pumping chamber. The logic then proceeds to a block 90, and Phase II is complete.

Figure 6:
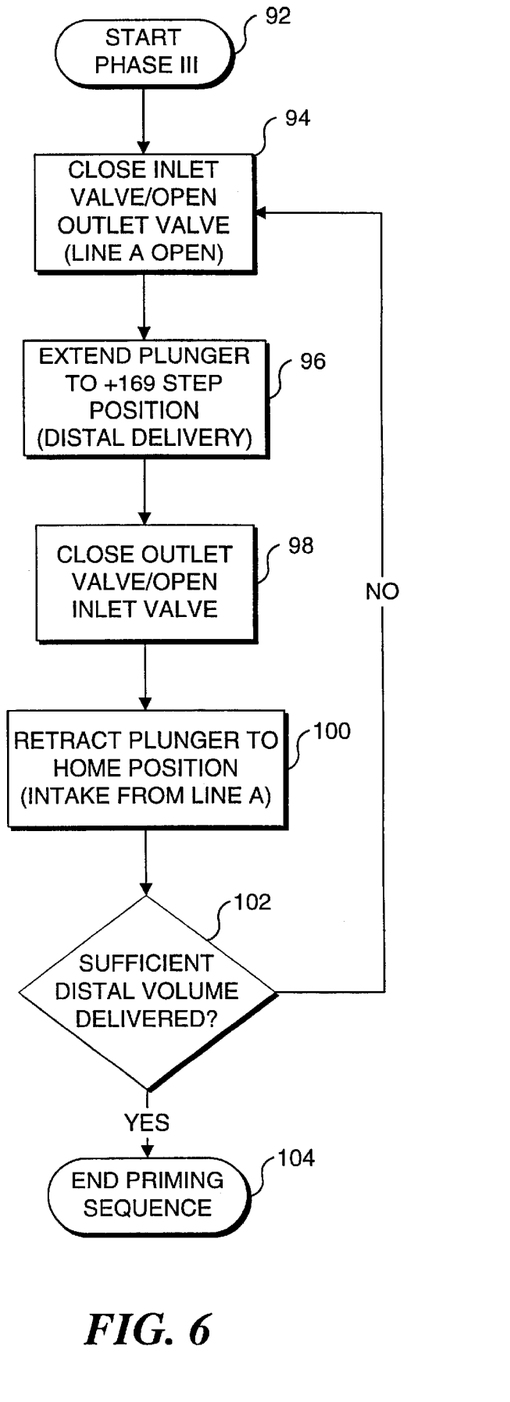
FIG. 6 is a flow chart illustrating the logical steps implemented to complete the third phase of the three-phase process of FIG. 2.

FIG. 6 illustrates the logical steps implemented to execute Phase III of the autoprime sequence, which delivers a fixed volume of liquid through outlet valve 26, removing air from pumping chamber 24 and the distal volume, thereby completing the autoprime sequence. The process begins at a start block 92. The logic proceeds to a block 94, and pump control unit 32 closes inlet valve 22 and opens outlet valve 26 (note that supply valve 14 remains in its open position). The logic then proceeds to a block 96, where pump control 32 extends the plunger to the +169 steps position, thereby distally delivering any fluid from within pumping chamber 24. The logic continues with a block 98, in which pump control unit 32 closes outlet valve 26 and opens inlet valve 22. A block 100 provides that the pump control unit 32 retracts the plunger to the home position, thereby drawing the standard intake volume of liquid (333 μl in the preferred embodiment) from liquid supply 12 into pumping chamber 24. A decision block 102 provides that the pump control 32 determines whether sufficient volume has been distally delivered. Because the distal volume is a known quantity, pump control 32 can determine if the most recent intake stroke provided sufficient liquid. For example. if the distal volume is less than 333 μl, and a normal intake stroke of 169 steps delivers 333 μl, then sufficient distal volume has been delivered. If the distal volume exceeds 333 μl, then pump control 32 can determine the number of steps required in the next intake stroke to deliver the remaining required volume. For example, if the distal volume is 400 μl, and 333 μl is delivered at block 96, then 67 μl will need to be delivered in the next pump cycle.

If sufficient volume has been delivered, then the logic advances to a block 104, and Phase III and the autopriming sequence are complete. If at decision block 102 pump control 32 determines that insufficient distal volume has been delivered, the logic returns to block 94, and the logical steps implemented in blocks 94–102 are repeated until sufficient volume has been delivered. It should be noted that the flowchart of FIG. 6 indicates that if, as described above, a 67 μl deficiency exists, then in block 96, the plunger will be extended to +169 strokes (a normal delivery stroke) and 333 μl of liquid will be delivered, which means that 266 μl more liquid will be distally delivered than required to prime the distal volume. An alternative to delivering substantially more liquid than required would be for pump control 32 to calculate the number of steps required to deliver the deficient volume, and to extend the plunger only by that number of steps, as opposed to a full 169 steps during the delivery stroke of the next pump cycle. In the example where there is a deficiency of 67 μl, 35 steps will deliver 68.95 μl, so pump control 32 can limit the plunger extension to 35 steps to ensure that sufficient volume is delivered, while minimizing wastage of medicinal liquid.

Although the present invention has been described in connection with the preferred form of practicing it and modifications thereto, those of ordinary skill in the art will understand that many other modifications can be made to the invention within the scope of the claims that follow. Accordingly, it is not intended that the scope of the invention in any way be limited by the above description, but instead be determined entirely by reference to the claims that follow.

The invention in which an exclusive right is claimed is defined by the following:

1. A method for priming a pump system that uses a cassette for infusing a liquid into a patient, so as to prevent air bubbles being delivered into a pumping chamber of the cassette, comprising the steps of:
   (a) introducing sufficient liquid into an air trap of the cassette such that a layer of the liquid separates an interior volume of the pumping chamber from an interior volume of the air trap;
   (b) back priming the pump system until air is removed from a proximal volume of the pump system; and
   (c) then forward priming the pump system until air is removed from the pumping chamber and from a distal volume of the pump system.

2. A method for priming a disposable cassette used for infusing a liquid into a patient so as to prevent a migration of air bubbles from an air trap into a pumping chamber of the disposable cassette, comprising the steps of:
   (a) introducing sufficient liquid into said air trap of said disposable cassette such that a layer of the liquid is deposited within the air trap, separating said pumping chamber from an interior volume of said air trap;
   (b) then introducing more liquid into the disposable cassette and pumping said more liquid from the disposable cassette in a proximal direction back toward a source of the liquid until no air is detected by a proximal air sensor within said disposable cassette; and
   (c) then introducing additional liquid into the disposable cassette, and pumping said additional liquid through the cassette in a distal direction until a desired volume of the additional liquid is distally delivered.

3. The method of claim 2, wherein the step of introducing sufficient liquid into said air trap comprises the steps of:
   (a) enabling the liquid to flow into the disposable cassette from the source of the liquid during successive pump cycles of the cassette until said proximal air sensor within said disposable cassette senses the liquid;
   (b) then stopping the pumping during a pump cycle of the cassette once said proximal air sensor senses the liquid; and
   (c) then pumping a predefined amount of the liquid into the air trap of the disposable cassette.

4. The method of claim 3, wherein the step of pumping the predefined amount of liquid into the disposable cassette comprises the step of pumping a volume of the liquid that approximates said interior volume of said air trap into the air trap of the disposable cassette.

5. The method of claim 2, wherein the step of introducing said more liquid into the disposable cassette and pumping said more liquid in the proximal direction comprises the step of introducing a full pump stroke of the liquid into the disposable cassette during each pump cycle.

6. The method of claim 5, wherein a volume of said full pump stroke of the liquid exceeds a proximal volume, and wherein the step of introducing said more liquid into the disposable cassette and pumping said more liquid in the proximal direction further comprises the step of introducing one full pump stroke of the liquid into the disposable cassette after no air is detected by said proximal air sensor, to ensure that any air within said proximal volume is discharged into the source of the liquid.

7. The method of claim 2, wherein said desired volume of the additional liquid exceeds a volume of a full pump stroke of the liquid, and wherein the step of introducing the additional liquid into the disposable cassette and pumping said additional liquid in the distal direction comprises the step of introducing a full pump stroke of the liquid into the disposable cassette during each pump cycle.

8. The method of claim 2, wherein said desired volume of additional liquid exceeds a volume of a full pump stroke of the liquid, and the step of introducing the additional liquid into the disposable cassette and pumping said additional liquid in the distal direction comprises the steps of introducing a full pump stroke of the liquid into the disposable cassette during each pump cycle until a difference between said desired volume of the additional liquid and an amount of the additional liquid already delivered is less than said volume of the full pump stroke of the liquid; and then introducing a partial pump stroke of the liquid into the disposable cassette, a volume of said partial pump stroke being substantially equal to said difference between said desired volume of the additional liquid and an amount of the additional liquid already delivered.

9. The method of claim 2, wherein said desired volume of additional liquid is less than a volume of a full pump stroke of the liquid, and the step of introducing the additional liquid into the disposable cassette and pumping said additional liquid in the distal direction comprises the step of introducing a full pump stroke of the liquid into the disposable cassette.

10. The method of claim 2, wherein said desired volume of the additional liquid is less than a volume of a full pump stroke of liquid, and the step of introducing the additional liquid into the disposable cassette and pumping said additional liquid in the distal direction comprises the step of introducing a partial pump stroke of the liquid into the disposable cassette, a volume of said partial pump stroke being substantially equal to said desired volume of the additional liquid.

11. A computer-readable medium having computer-executable instructions for performing the steps recited in claim 2.

12. A method of priming a cassette used in an infusion pump system for infusing a liquid into a patient, which substantially prevents an accumulation of air bubbles within a pumping chamber of the cassette, comprising the steps of:
  (a) providing a cassette having a housing that defines a liquid path between an inlet port adapted to couple in fluid communication with a source, and an outlet port adapted to couple in fluid communication with an infusion site on the patient, said cassette also including an inlet air sensor that produces a signal indicative of a presence of air proximate the inlet port, said liquid path within the cassette including:
    (i) a pumping chamber covered by an elastomeric membrane that when forced into the pumping chamber by a driven member displaces the liquid from the pumping chamber through one of said inlet port and said outlet port; and
    (ii) an air trap disposed between said inlet air sensor and said pumping chamber;
  (b) introducing sufficient liquid into said air trap of said cassette such that a layer of liquid disposed within the air trap separates said pumping chamber from an interior volume of said air trap; said layer of liquid acting as a one-way valve that allows air from said pumping chamber to pass into said air trap, while preventing air from said air trap from passing into said pumping chamber;
  (c) back priming the cassette to remove air from a proximal volume of the infusion pump system; and
  (d) forward priming the cassette to remove air from said pumping chamber and a distal volume of the infusion pump system.

13. The method of claim 12, wherein the step of introducing sufficient liquid into said air trap of said cassette comprises the step of producing said layer of liquid at a bottom of said air trap, such that said layer of liquid substantially covers said bottom of said air trap.

14. The method of claim 12, wherein the step of introducing sufficient liquid into said air trap of said cassette comprises the steps of:
  (a) pumping liquid from the source toward the cassette, using strokes of the driven member that deliver a standard volume of liquid during each pump cycle, until said inlet air sensor does not detect air; and
  (b) then enabling an additional pump cycle to occur, using an extra long stroke of the driven member that delivers more than the standard volume of liquid from the source to the cassette in said additional pump cycle.

15. The method of claim 14, wherein the extra long stroke delivers a volume of liquid that substantially equals said interior volume of said air trap.

16. The method of claim 12, wherein the step of introducing sufficient liquid into said air trap of said cassette comprises the step of introducing a volume of liquid that has been empirically determined to generate the layer of the liquid within said air trap, of a desired size.

17. The method of claim 12, wherein the step of back priming the cassette to remove air from the proximal volume comprises the steps of:
  (a) pumping in a reverse direction, using strokes that deliver a standard volume of liquid in each pump cycle, until said inlet air sensor does not detect air; and
  (b) pumping one additional cycle in said reverse direction, using a stroke that delivers said standard volume of liquid in said one additional cycle.

18. The method of claim 12, wherein the step of forward priming the cassette to remove air from said pumping chamber and the distal volume comprises the step of pumping the liquid in a forward direction, until a volume of liquid larger than said distal volume is delivered.

19. A computer-readable medium having computer-executable instructions for performing the steps recited in claim 12.

20. A pump system that substantially prevents air bubbles from being trapped within a pumping chamber during priming of the pump system, said pump system being employed to infuse a liquid flowing from a source into an infusion site at a patient, comprising:
  (a) a cassette having a housing that defines a liquid path from an inlet port that is adapted to couple in fluid communication with the source, to an outlet port that is adapted to couple in fluid communication with the infusion site, said liquid path being disposed within the cassette and including:
    (i) a pumping chamber covered by an elastomeric membrane that when forced into the pumping chamber, displaces liquid from the pumping chamber through one of said inlet port and said outlet port;
    (ii) an inlet air sensor that produces a signal indicative of a presence of air proximate said inlet port; and
    (iii) an air trap disposed between said inlet air sensor and said pumping chamber;
  (b) a proximal liquid line that provides fluid communication between said source and said inlet port;
  (c) a distal liquid line, a first end of said distal liquid line being in fluid communication with said outlet port, and a second end of said distal liquid line being adapted to couple to said infusion site;
  (d) a drive unit adapted to couple with said cassette and including at least one prime mover and a plunger, said at least one prime mover moving the plunger relative to the pumping chamber to deform the elastomeric membrane, a deformation of the elastomeric membrane into the pumping chamber displacing liquid from the pumping chamber toward one of said inlet port and said outlet port; and
  (e) a control unit, coupled to receive the signals from said air sensor, and coupled to the drive unit to control said at least one prime mover and thereby controlling movement of the plunger, said control unit including a processor coupled to a memory in which machine instructions are stored, said machine instructions, when executed by the processor, causing the processor to establish a layer of liquid within said air trap to separate an interior volume of said air trap from said pumping chamber before priming the cassette, thereby preventing air bubbles from said air trap from entering into said pumping chamber.

21. The pump system of claim 20, wherein a volume of liquid displaced from said pumping chamber during a normal pump cycle exceeds a total volume of said proximal liquid line and a portion of said liquid path between said inlet port and said air sensor.

22. A pump system for substantially preventing air bubbles from being trapped in a pumping chamber during priming of said pump system, said pump system being employed for producing a liquid flow through an intravenous line, comprising:
  (a) a pump chassis;
  (b) a pump in fluid communication with the intravenous line and mountable within the pump chassis to receive a driving force from a driven member that is included in the pump chassis, said pump including:
    (i) an inlet port;
    (ii) an outlet port; and
    (iii) a liquid path that includes the pumping chamber and extends between the inlet port and outlet port, said driven member displacing the liquid from said pumping chamber and into one of said inlet port and outlet port;
  (c) an air sensor disposed proximate said inlet port, said air sensor producing a signal indicative of a presence of air;
  (d) an air trap disposed in said liquid path between said pumping chamber and said inlet port; and
  (e) a controller disposed within the pump chassis and electrically coupled to said air sensor to receive signals therefrom during a pump cycle, said controller operating the pump before initiating a priming sequence to produce a layer of liquid within said air trap, said layer of liquid separating said air trap from said pumping chamber and preventing air from moving from said air trap to said pumping chamber, but allowing air from said pumping chamber to move into said air trap.

23. An autopriming pump system that substantially prevents air bubbles from being trapped within a pumping chamber when the pump system is autoprimed, comprising:
  (a) a pump unit having an outlet at a distal end and an inlet at a proximal end, a liquid path connecting said distal end to said proximal end, said liquid path including
    (i) said pumping chamber, liquid driven from said pumping chamber by the pump being selectively driven in one of a proximal direction and a distal direction;
    (ii) an air sensor disposed proximate said proximal end, said air sensor producing a signal indicative of a presence of air proximate said proximal end; and
    (iii) an air trap disposed between said air sensor and said pumping chamber;
  (b) a liquid supply in fluid communication through a proximal liquid with the inlet at said proximal end of said pump unit, said proximal liquid line defining a proximal volume that is less than a volume of liquid expelled from the pumping chamber in said pump unit during a single pump cycle;
  (c) a drive unit drivingly connected to said pump unit to provide a force that drives liquid from the pumping chamber during a pump cycle; and
  (d) a control unit electrically coupled to said drive unit and said air sensor, said control unit controlling a flow of liquid through said pump system, said control unit including a processor coupled to a memory in which machine instructions are stored, said machine instructions being executed by the processor and causing the processor to:
    (i) control said flow of liquid that is pumped by the pump unit to establish a layer of liquid within said air trap, said layer of liquid separating an interior volume of said air trap from said pumping chamber, thereby substantially preventing air bubbles from said air trap from entering said pumping chamber;
    (ii) control said flow of liquid that is pumped by said pump unit to back prime said pumping system, until air is removed from said proximal liquid line, and
    (iii) control said flow of liquid that is pumped by said pump unit to forward prime said pumping system, until air is removed from said pumping chamber and a portion of said liquid path between said pumping chamber and said distal end of said pump unit.

* * * * *

UNITED STATES PATENT AND TRADEMARK OFFICE
CERTIFICATE OF CORRECTION

PATENT NO. : 6,475,178 B1
DATED : November 5, 2002
INVENTOR(S) : David A. Krajewski et al.

It is certified that error appears in the above-identified patent and that said Letters Patent is hereby corrected as shown below:

<u>Title page,</u>
Item [75], Inventors, replace "David J. Krajewski" with -- David A. Krajewski --.

Signed and Sealed this

Eighth Day of July, 2003

JAMES E. ROGAN
*Director of the United States Patent and Trademark Office*